(12) United States Patent
Gandhi et al.

(10) Patent No.: US 8,333,798 B2
(45) Date of Patent: Dec. 18, 2012

(54) IMPLANTABLE MEDICAL DEVICES WITH ENHANCED VISIBILITY, MECHANICAL PROPERTIES AND BIOCOMPATABILITY

(75) Inventors: Deepak Gandhi, Los Angeles, CA (US); Leon Rudakov, San Marcos, CA (US); Michael O'Connor, Singapore (SG)

(73) Assignee: Merlin MD Pte Ltd., Singapore (SG)

( * ) Notice: Subject to any disclaimer, the term of this patent is extended or adjusted under 35 U.S.C. 154(b) by 1122 days.

(21) Appl. No.: 10/578,806

(22) PCT Filed: Sep. 30, 2004

(86) PCT No.: PCT/SG2004/000319
§ 371 (c)(1),
(2), (4) Date: May 8, 2006

(87) PCT Pub. No.: WO2005/044361
PCT Pub. Date: May 19, 2005

(65) Prior Publication Data
US 2007/0067009 A1    Mar. 22, 2007

(30) Foreign Application Priority Data
Nov. 7, 2003  (SG) ............... 200306809-5

(51) Int. Cl.
*A61F 2/82* (2006.01)
(52) U.S. Cl. ..................... 623/1.15; 623/1.34
(58) Field of Classification Search .......... 623/1.15, 623/1.34; *A61F 2/82*
See application file for complete search history.

(56) References Cited

U.S. PATENT DOCUMENTS

| | | | |
|---|---|---|---|
| 4,503,569 A | 3/1985 | Dotter | |
| 4,733,665 A * | 3/1988 | Palmaz | 606/108 |
| 5,041,441 A | 8/1991 | Radin et al. | |
| 5,234,457 A | 8/1993 | Andersen | |
| 5,356,423 A | 10/1994 | Tihon et al. | |
| 5,405,377 A | 4/1995 | Cragg | |
| D359,802 S | 6/1995 | Fontaine | |
| 5,421,955 A | 6/1995 | Lau et al. | |
| 5,443,458 A | 8/1995 | Eury | |
| 5,514,154 A | 5/1996 | Lau et al. | |
| 5,562,725 A | 10/1996 | Schmitt et al. | |
| 5,589,563 A | 12/1996 | Ward et al. | |

(Continued)

FOREIGN PATENT DOCUMENTS
EP          0754435         1/1997
(Continued)

OTHER PUBLICATIONS
"A Hysteresis-free platinum alloy flexure material for improved performanc enad reliability fo MEMS devices"; Brazzle, J.D. et al.; Transducerrs '03 pp. 1152-2 vol. 2.*

(Continued)

*Primary Examiner* — Christopher D Koharski
*Assistant Examiner* — Jason-Dennis Stewart
(74) *Attorney, Agent, or Firm* — James W. Hill; M. Todd Hales; McDermott Will & Emery LLP (57) ABSTRACT

An implantable mechanical device for insertion into a passage, where the device is made from a platinum alloy selected from the group consisting of platinum:iridium alloy, platinum:tungsten alloy, platinum:rhodium:ruthenium alloy, platinum:rhodium alloy and platinum:nickel alloy.

20 Claims, 4 Drawing Sheets

U.S. PATENT DOCUMENTS

| | | | |
|---|---|---|---|
| 5,601,593 A | 2/1997 | Freitag | |
| 5,620,763 A | 4/1997 | House et al. | |
| 5,630,840 A | 5/1997 | Mayer | |
| 5,632,840 A | 5/1997 | Campbell | |
| 5,639,278 A | 6/1997 | Dereume et al. | |
| 5,700,285 A | 12/1997 | Myers et al. | |
| D390,957 S | 2/1998 | Fontaine | |
| 5,718,973 A | 2/1998 | Lewis et al. | |
| 5,733,330 A * | 3/1998 | Cox | 623/1.15 |
| 5,735,893 A | 4/1998 | Lau et al. | |
| 5,744,515 A | 4/1998 | Clapper | |
| 5,766,238 A | 6/1998 | Lau et al. | |
| 5,769,884 A | 6/1998 | Solovay | |
| 5,810,870 A | 9/1998 | Myers et al. | |
| 5,843,172 A | 12/1998 | Yan | |
| 5,858,556 A | 1/1999 | Eckert et al. | |
| 5,866,217 A | 2/1999 | Stenoien et al. | |
| 5,902,475 A | 5/1999 | Trozera et al. | |
| 5,925,075 A | 7/1999 | Myers et al. | |
| 5,948,018 A | 9/1999 | Dereume et al. | |
| 5,951,599 A | 9/1999 | McCrory | |
| 5,993,489 A | 11/1999 | Lewis et al. | |
| 6,001,123 A | 12/1999 | Lau | |
| 6,010,530 A | 1/2000 | Goicoechea | |
| 6,024,765 A | 2/2000 | Wallace et al. | |
| 6,027,811 A | 2/2000 | Campbell et al. | |
| 6,033,435 A | 3/2000 | Penn et al. | |
| 6,036,720 A | 3/2000 | Abrams et al. | |
| 6,056,776 A | 5/2000 | Lau et al. | |
| 6,066,167 A | 5/2000 | Lau et al. | |
| 6,139,564 A | 10/2000 | Teoh | |
| 6,140,127 A | 10/2000 | Sprague | |
| 6,168,610 B1 | 1/2001 | Marin et al. | |
| 6,174,328 B1 | 1/2001 | Cragg | |
| 6,217,607 B1 | 4/2001 | Alt | |
| 6,240,616 B1 | 6/2001 | Yan | |
| 6,240,948 B1 | 6/2001 | Hansen, III et al. | |
| 6,248,190 B1 | 6/2001 | Stinson | |
| 6,309,367 B1 | 10/2001 | Boock | |
| 6,312,463 B1 | 11/2001 | Rourke et al. | |
| 6,315,791 B1 | 11/2001 | Gingras et al. | |
| 6,409,754 B1 | 6/2002 | Smith et al. | |
| 6,416,474 B1 | 7/2002 | Penner et al. | |
| 6,451,050 B1 | 9/2002 | Rudakov et al. | |
| 6,451,052 B1 | 9/2002 | Burmeister et al. | |
| 6,454,780 B1 | 9/2002 | Wallace | |
| 6,485,507 B1 | 11/2002 | Walak et al. | |
| 6,488,701 B1 | 12/2002 | Nolting et al. | |
| 6,508,832 B1 | 1/2003 | Jalisi et al. | |
| 6,517,571 B1 | 2/2003 | Brauker et al. | |
| 6,527,802 B1 | 3/2003 | Mayer | |
| 6,533,905 B2 | 3/2003 | Johnson et al. | |
| 6,547,815 B2 | 4/2003 | Myers | |
| 6,572,648 B1 * | 6/2003 | Klumb et al. | 623/1.15 |
| 6,582,461 B1 | 6/2003 | Burmeister et al. | |
| 6,582,652 B2 | 6/2003 | Craig | |
| 6,613,072 B2 | 9/2003 | Lau et al. | |
| 6,623,520 B2 | 9/2003 | Jalisi | |
| 6,652,574 B1 | 11/2003 | Jayaraman | |
| D484,979 S | 1/2004 | Fontaine | |
| 6,673,108 B2 | 1/2004 | Zilla et al. | |
| 6,676,701 B2 | 1/2004 | Rourke et al. | |
| 6,679,910 B1 | 1/2004 | Granada | |
| 6,695,833 B1 | 2/2004 | Frantzen | |
| 6,695,876 B1 | 2/2004 | Marotta et al. | |
| 6,699,276 B2 | 3/2004 | Sogard et al. | |
| 6,706,061 B1 | 3/2004 | Fischell et al. | |
| 6,719,782 B1 | 4/2004 | Chuter | |
| 6,736,844 B1 | 5/2004 | Glatt et al. | |
| 6,767,360 B1 * | 7/2004 | Alt et al. | 623/1.15 |
| 6,802,851 B2 | 10/2004 | Jones et al. | |
| 6,818,013 B2 | 11/2004 | Mitelberg et al. | |
| 6,821,293 B2 | 11/2004 | Pinchasik | |
| 6,855,154 B2 | 2/2005 | Abdel-Gawwad | |
| 6,899,727 B2 | 5/2005 | Armstrong et al. | |
| 6,936,055 B1 | 8/2005 | Ken et al. | |
| 6,949,116 B2 | 9/2005 | Solymar et al. | |
| 6,979,349 B1 | 12/2005 | Dang et al. | |
| 7,029,493 B2 | 4/2006 | Majercak et al. | |
| 7,041,129 B2 | 5/2006 | Rourke et al. | |
| 7,060,091 B2 | 6/2006 | Killion et al. | |
| 7,105,019 B2 | 9/2006 | Hojeibane | |
| 7,153,322 B2 | 12/2006 | Alt | |
| 7,169,174 B2 | 1/2007 | Fischell et al. | |
| D553,746 S | 10/2007 | Fliedner | |
| D553,747 S | 10/2007 | Fliedner | |
| 7,306,622 B2 | 12/2007 | Jones et al. | |
| 7,311,726 B2 | 12/2007 | Mitelberg et al. | |
| 2002/0035394 A1 | 3/2002 | Fierens et al. | |
| 2002/0042646 A1 | 4/2002 | Wall | |
| 2002/0045931 A1 | 4/2002 | Sogard et al. | |
| 2002/0049495 A1 | 4/2002 | Kutryk et al. | |
| 2002/0065546 A1 | 5/2002 | Machan et al. | |
| 2002/0111543 A1 | 8/2002 | Penner et al. | |
| 2002/0151968 A1 | 10/2002 | Zilla et al. | |
| 2003/0009215 A1 * | 1/2003 | Mayer | 623/1.22 |
| 2003/0018294 A1 | 1/2003 | Cox | |
| 2003/0060782 A1 | 3/2003 | Bose et al. | |
| 2003/0093111 A1 | 5/2003 | Ken | |
| 2003/0171801 A1 | 9/2003 | Bates | |
| 2003/0181973 A1 * | 9/2003 | Sahota | 623/1.15 |
| 2003/0229286 A1 | 12/2003 | Lenker | |
| 2003/0229393 A1 | 12/2003 | Kutryk et al. | |
| 2003/0233141 A1 | 12/2003 | Israel | |
| 2004/0029268 A1 | 2/2004 | Colb et al. | |
| 2004/0039438 A1 * | 2/2004 | Alt | 623/1.15 |
| 2004/0087998 A1 | 5/2004 | Lee et al. | |
| 2004/0116998 A1 | 6/2004 | Erbel et al. | |
| 2004/0170685 A1 | 9/2004 | Carpenter et al. | |
| 2004/0172121 A1 | 9/2004 | Eidenschink et al. | |
| 2004/0186562 A1 | 9/2004 | Cox | |
| 2004/0193206 A1 | 9/2004 | Gerberding et al. | |
| 2004/0193246 A1 * | 9/2004 | Ferrera | 623/1.15 |
| 2005/0043787 A1 | 2/2005 | Kutryk et al. | |
| 2005/0075716 A1 | 4/2005 | Yan | |
| 2005/0096725 A1 | 5/2005 | Pomeranz et al. | |
| 2005/0124896 A1 | 6/2005 | Richter et al. | |
| 2005/0137677 A1 | 6/2005 | Rush | |
| 2005/0137680 A1 | 6/2005 | Ortiz et al. | |
| 2005/0154448 A1 | 7/2005 | Cully et al. | |
| 2005/0171593 A1 | 8/2005 | Whirley et al. | |
| 2005/0267568 A1 | 12/2005 | Berez et al. | |
| 2005/0283220 A1 | 12/2005 | Gobran et al. | |
| 2006/0020322 A1 | 1/2006 | Leynov et al. | |
| 2006/0036311 A1 | 2/2006 | Nakayama et al. | |
| 2006/0106421 A1 | 5/2006 | Teoh | |
| 2006/0121080 A1 | 6/2006 | Lye et al. | |
| 2006/0136037 A1 | 6/2006 | DeBeer et al. | |
| 2006/0142849 A1 | 6/2006 | Killion et al. | |
| 2006/0149355 A1 | 7/2006 | Mitelberg et al. | |
| 2006/0155355 A1 | 7/2006 | Jung | |
| 2006/0173530 A1 | 8/2006 | Das | |
| 2006/0200230 A1 | 9/2006 | Richter | |
| 2006/0200234 A1 | 9/2006 | Hines | |
| 2006/0206199 A1 | 9/2006 | Churchwell et al. | |
| 2006/0217799 A1 | 9/2006 | Mailander et al. | |
| 2006/0224237 A1 | 10/2006 | Furst et al. | |
| 2006/0259123 A1 | 11/2006 | Dorn | |
| 2006/0265051 A1 | 11/2006 | Caro et al. | |
| 2006/0276877 A1 | 12/2006 | Owens et al. | |
| 2006/0276878 A1 | 12/2006 | Owens et al. | |
| 2006/0276879 A1 | 12/2006 | Lye et al. | |
| 2006/0287710 A1 | 12/2006 | Lendlein et al. | |
| 2007/0038288 A1 | 2/2007 | Lye et al. | |
| 2007/0083258 A1 | 4/2007 | Falotico et al. | |
| 2007/0088387 A1 | 4/2007 | Eskridge et al. | |
| 2007/0112415 A1 | 5/2007 | Bartlett | |
| 2007/0213800 A1 | 9/2007 | Fierens et al. | |
| 2007/0276477 A1 | 11/2007 | Lee et al. | |
| 2007/0288083 A1 | 12/2007 | Hines | |
| 2008/0004653 A1 | 1/2008 | Sherman et al. | |
| 2009/0054966 A1 | 2/2009 | Rudakov et al. | |

FOREIGN PATENT DOCUMENTS

| | | |
|---|---|---|
| EP | 0864301 | 9/1998 |
| EP | 0947204 | 10/1999 |
| EP | 1057460 A1 | 12/2000 |

| | | |
|---|---|---|
| EP | 1121911 | 8/2001 |
| EP | 1129666 | 9/2001 |
| EP | 1391184 | 2/2004 |
| EP | 1 470 795 | 10/2004 |
| EP | 1543798 | 6/2005 |
| EP | 1550477 | 7/2005 |
| EP | 1797844 | 6/2007 |
| JP | 1254623 | 10/1989 |
| WO | WO 9814137 | 4/1998 |
| WO | WO 99/02092 | 1/1999 |
| WO | WO 99/58084 | 11/1999 |
| WO | WO 99/62432 | 12/1999 |
| WO | WO 00/01308 | 1/2000 |
| WO | WO 00/06145 | 2/2000 |
| WO | WO 00/47134 | 8/2000 |
| WO | WO 00/51522 | 9/2000 |
| WO | WO 00/56247 | 9/2000 |
| WO | WO 01/03607 | 1/2001 |
| WO | WO 01/66167 | 9/2001 |
| WO | WO 01/87184 | 11/2001 |
| WO | WO 01/93782 | 12/2001 |
| WO | WO 02/22024 | 3/2002 |
| WO | WO 02-051336 | 7/2002 |
| WO | WO 02/69783 | 9/2002 |
| WO | WO 02/078764 | 10/2002 |
| WO | WO 03/49600 | 6/2003 |
| WO | WO 03/065881 | 8/2003 |
| WO | WO 2004-000379 | 12/2003 |
| WO | WO 2004-028405 | 4/2004 |
| WO | WO 2005/000165 | 1/2005 |
| WO | WO 2005-065580 | 7/2005 |
| WO | WO 2005-086831 | 9/2005 |
| WO | WO 2005/094725 | 10/2005 |
| WO | WO 2005/094726 | 10/2005 |
| WO | WO 2006/033641 | 3/2006 |

OTHER PUBLICATIONS

"Resistance to fatigue crack growth of the platinum metals"; Speidel, Markus O.; Platinum Metals Review 1981 25/1 (24-31).*

Reul, J. et al., Long-Term Angiographic and Histopathalogic Findings in Experimental Aneurysms of the Carotid Bifurcation Embolized with Platinum and Tungsten Coils, American Journal of Neuroradiology, Jan. 1997, pp. 35-42, vol. 18.

Chatterjee, S., Lactosylceramide stimulates aortic smooth muscle cell proliferation, Biochemical and Biophysical Research Communications, Dec. 16, 1991, 554-561, vol. 181, No. 2, Academic Press, Orlando FL.

* cited by examiner

ICA & Circle of Willis Arteries

FIG. 4

IMPLANTABLE MEDICAL DEVICES WITH ENHANCED VISIBILITY, MECHANICAL PROPERTIES AND BIOCOMPATABILITY

CROSS-REFERENCE TO OTHER APPLICATIONS

This is a National Phase of International Application No. PCT/SG2004000319, filed on Sep. 30, 2004, which claims priority from Singaporean Patent Application No. 200306809-5, filed on Nov. 7, 2003.

TECHNICAL FIELD

The present invention concerns an implantable medical device suitable for intravascular applications.

BACKGROUND OF THE INVENTION

Vascular diseases include aneurysms which can rupture and cause hemorrhage, atherosclerosis which can cause the occlusion of the blood vessels, vascular malformation and tumors. Vessel occlusion or rupture of an aneurysm within the brain are common causes of stroke. Tumors fed by intracranial arteries can grow within the brain to a point where their mass and size can cause a stroke or the symptoms of stroke, requiring surgery for removal of the tumors or other remedial intervention.

Occlusion of the coronary arteries, for example, is a common cause of heart attack. Diseased and obstructed coronary arteries can restrict the flow of blood in the heart and cause tissue ischemia and necrosis. While the exact etiology of sclerotic cardiovascular disease is still in question, the treatment of narrowed coronary arteries is more defined. Surgical construction of coronary artery bypass grafts (CABG) is often the method of choice when there are several diseased segments in one or multiple arteries. Conventional open-heart surgery is, of course, very invasive and traumatic for patients undergoing such treatment. Therefore, alternative methods being less traumatic are highly desirable.

One of the alternative methods is balloon angioplasty that is a technique in which a folded balloon is inserted into a stenosis which occludes or partially occludes an artery and is inflated to open the occluded artery. Another alternative method is atherectomy that is a technique in which occlusive atheromas are cut from the inner surface of the arteries. Both methods suffer from reocclusion with certain percentage of patients.

One therapy for vascular occlusions is placement of an expandable metal wire-frame including stent, within the occluded region of blood vessel to hold it open. The stent is delivered to the desired location within a vascular system by a delivery means, usually a catheter. Some advantages of the stent-placement method over conventional vascular surgery include obviating the need for surgically exposing, removing, replacing, or by-passing the defective blood vessel, including heart-lung by-pass, opening the chest, and general anaesthesia.

When inserted and deployed in a vessel, duct or tract ("vessel") of an organic body, for example a coronary artery after dilatation of the artery by balloon angioplasty, a stent acts as a prosthesis to maintain the vessel open. The stent usually has an open-ended tubular form with interconnected struts as its sidewall to enable its expansion from a first outside diameter which is sufficiently small to allow the stent to traverse the vessel to reach a site where it is to be deployed, to a second outside diameter sufficiently large to engage the inner lining of the vessel for retention at the site. A stent is typically delivered in an unexpanded state to a desired location in a body lumen and then expanded. The stent may be expanded via the use of a mechanical device such as a balloon, or the stent may be self-expanding.

Stents are typically made from biocompatible metals such as stainless steel, nickel-titanium, cobalt-chromium, tantalum, and the like, which provide sufficient hoop strength to perform the scaffolding function. Furthermore, stents have a minimal wall thickness in order to minimize blood flow blockage. Stents of various construction have been proposed, including the Palmaz-Schatz® balloon expandable metal stent, the Wallstent self-expanding braided metal stent, the Strecker knitted metal stent, the Instent® coil stent, the Cragg coiled stent and the Gianturco Z stent. However, stents can sometimes cause complications including thrombosis and neointimal hyperplasia, such as by inducement of smooth muscle cell proliferation at the site of implantation of the stent.

A factor affecting the choice of stent and stent material is allergic reaction to common stent materials suffered by a statistically significant percentage of the patient population subjected to stenting. These materials include chrome, nickel, and medical 316L stainless steel containing about 16% nickel.

Another consideration in material selection is the need for a physician to be able to visualize the position of a stent during implantation to the desired target site in an organic body, and for purpose of examination from time to time thereafter at the implant site, typically by X-ray fluoroscopy. The sidewall of the stent must be sufficiently thick, depending on the stent material, not only to withstand the vessel wall recoil that invariably follows deployment at the target site, but to allow the stent to be seen on the fluoroscope. Various materials, such as 316L stainless steel, possess suitable mechanical strength, however the X-ray absorption of the metal is low. The fluoroscopic visibility of stainless steel, for example, in a thickness below 100 μm is very poor because of the limited extinction of x-rays by such a thin metal tube. In addition, increasing the sidewall thickness of a stent to enhance its radiopacity and recoil resistance makes the stent less flexible. On the other hand, the thinner the stent strut, the less the lumen of the stented vessel is obstructed. Moreover, a thin stent is covered more readily by a neoendothelial build-up. Thus, it is desirable to make the sidewall of a stent as thin as can be practically achieved, without compromising the strength or visibility of the stent.

SUMMARY OF THE INVENTION

In a first preferred aspect, there is provided an implantable medical device for insertion into a passage, wherein the device is made from a platinum alloy selected from the group consisting of platinum:iridium alloy, platinum tungsten alloy, platinum:rhodium:ruthenium alloy, platinum:rhodium alloy and platinum:nickel alloy.

Advantageously, an implantable medical device for successful interventional placement is provided which possesses the features of biocompatibility to avoid of vessel re-occlusion, relatively non-allergenic reaction, enhanced radiopacity, freedom from distortion on magnetic resonance imaging (MRI), flexibility with suitable elasticity to be plastically deformable, strong resistance to vessel recoil, and sufficient thinness to minimize obstruction to flow of blood (or other fluid or material in vessels other than the cardiovascular system). The selection of the material of which a stent is composed, as well as design of the stent, plays an important role in influencing these features.

The passage may be a bodily vessel such as a vascular vessel.

The device may be an expandable device. The expandable device may be a stent. The stent may comprise a generally tubular structure having an exterior surface defined by a plurality of interconnected struts having interstitial spaces therebetween, said generally tubular structure expandable from a first position to a second position, wherein said tubular structure expands radially outwardly to the second position such that the exterior surface of said structure engages with the inner surface of the bodily vessel so as to maintain a fluid pathway through said bodily vessel.

The stent may be a self-expandable stent. The stent may be expandable by balloon inflation.

Preferably, the platinum:iridium alloy has a composition of about 60-90% of platinum and 10-40% of iridium. More preferably, the platinum:iridium alloy has a composition of about 70-90% of platinum and 10-30% iridium. Even more preferably, the platinum:iridium alloy has a composition of about 70-80% of platinum and 20-30% iridium.

Preferably, the platinum:tungsten alloy has a composition of about 85-95% of platinum and 5-15% of tungsten. More preferably, the platinum:tungsten alloy has a composition of about 90-95% of platinum and 5-10% of tungsten.

Preferably, the platinum:rhodium:ruthenium alloy has a composition of about 70-85% of platinum, 10-20% of rhodium and 3-10% of ruthenium. More preferably, the platinum:rhodium:ruthenium alloy has a composition of about 75-80% of platinum, 12-18% of rhodium and 5-10% of ruthenium.

Preferably, the platinum:rhodium alloy has a composition of about 60-80% of platinum and 20-40% of rhodium. More preferably, the platinum:rhodium alloy has a composition of about 65-75% of platinum and 25-35% of rhodium.

Preferably, the platinum:nickel alloy has a composition of about 80-90% of platinum and 10-20% of nickel. More preferably, the platinum:nickel alloy has a composition of about 85-90% of platinum and 10-15% of nickel.

The device may be made from a wire of platinum:tungsten, platinum:iridium alloys, and welded to a predetermined tubular mesh.

The device may have a sidewall thickness of less than 0.0035".

The surface of the device may be modified by passive coatings. The device may be coated with an external layer containing a pharmaceutically effective amount of therapeutic substances.

In a second aspect, there is provided an implantable endovascular device for insertion into a bodily vessel to treat ischemic and hemorrhagic stroke, the device comprising:
a wire structure made from a platinum alloy selected from the group consisting of platinum:iridium alloy and platinum:tungsten alloy, the structure being expandable from a first position to a second position, and said structure expands radially outwardly to the second position such that an exterior surface of said structure engages with the inner surface of the bodily vessel so as to maintain a fluid pathway through said bodily vessel;
wherein the wire structure is formed by welding tubular shaped wire sections together and the exterior surface of the wire structure is defined by the welded wire sections.

In a third aspect, there is provided a delivery system for inserting a device an implantable medical device as described, within a bodily vessel, wherein the device is expandable by balloon inflation, the delivery system comprising a balloon delivery catheter and the device, wherein the expandable medical device is mounted onto the balloon of the delivery catheter.

In a fourth aspect, there is provided a delivery system for inserting an implantable medical device as described, within a bodily vessel, wherein the device is self-expandable, the delivery system comprising a delivery catheter and the device, wherein the device is mounted onto a distal portion of the delivery catheter.

The stent may be deployed at a pressure equal to or below 4 atm.

The stent may be longitudinally flexible, the flexibility being such that it is greater than a delivery catheter to deliver the stent into the bodily vessel. The longitudinal flexibility may be defined by deflection of the device from a neutral line to 1 mm when there is a force less then 8 grams.

The structure of the device may provide a normalized radial force 18 to 19 grams per mm of length. The structural support of the device may provide 3 to 4% of deflection of the structure of the device together with natural pulsing of an intracranial vessel wall.

The device may have a profile in a compressed delivery form of 0.020 inches. The device may have a profile between 0.014 to 0.016 inches and a profile in an uncompressed delivery form may be between 0.020 to 0.022 inches.

The device may have uniform material distribution and wall coverage for providing support to a bodily vessel. The ratio of the material may be in the range of 12 to 16%, the range being dependent on the diameter of deployment.

The device may comprise struts, the struts having a thickness and width less than or equal to 0.0028 inches. The device may have a surface to length ratio between 1.1 to 1.3 $mm^2/mm$ to provide minimal vessel injury score.

It is an advantage of at least one embodiment of the present invention to provide an implantable medical device that has enhanced biocompatibility, visibility, excellent mechanical properties and a low profile. The present invention provides implantable medical devices that are made from platinum: iridium, platinum:tungsten, and other platinum alloys.

BRIEF DESCRIPTION OF THE DRAWINGS

An example of the invention will now be described with reference to the accompanying drawings, in which.

DETAILED DESCRIPTION OF THE DRAWINGS

Throughout this application, where publications are referenced, the disclosures of these publications are hereby incorporated by reference, in their entireties, into this application in order to more fully describe the state of art to which this invention pertains.

Stents are expandable prostheses employed to maintain vascular and endoluminal ducts or tracts of the human body open and unoccluded, such as a portion of the lumen of a coronary artery after dilatation of the artery by balloon angioplasty. While vascular usage is discussed in detail in this application, it will be understood by those skilled in the art that stents having the characteristics and features of the present invention may be implanted in other ducts or tracts of the human body to keep the lumen open, such as in the cerebral circulation system, tracheo-bronchial system, the biliary hepatic system, the esophageal bowel system, and the urinary tract system. It is also noted that while stents are typical medical devices used for implantation, implantable medical devices that are made from the disclosed alloys of the present invention and used in different applications are not so limited, including vena cava filters, grafts or aneurysm coils.

A typical stent is a generally tubular structure having an exterior surface defined by a plurality of interconnected struts having interstitial spaces there between. The generally tubular structure is expandable from a first position, wherein the stent is sized for intravascular insertion, to a second position, wherein at least a portion of the exterior surface of the stent contacts the vessel wall. The expanding of the stent is accommodated by flexing and bending of the interconnected struts throughout the generally tubular structure. It is contemplated that many different stent designs can be produced. An intricate pattern of interconnecting struts can be produced that enable the stent to expand radially when subjected to the appropriate radially directed forces such as are exerted by the inflation of an underlying balloon. A myriad of strut patterns are known for achieving various design goals such as enhancing strength, maximizing the expansion ratio or coverage area, enhancing longitudinal flexibility or longitudinal stability upon expansion, etc. One pattern may be selected over another in an effort to optimize those parameters that are of particular importance for a particular application.

Figure 1A:
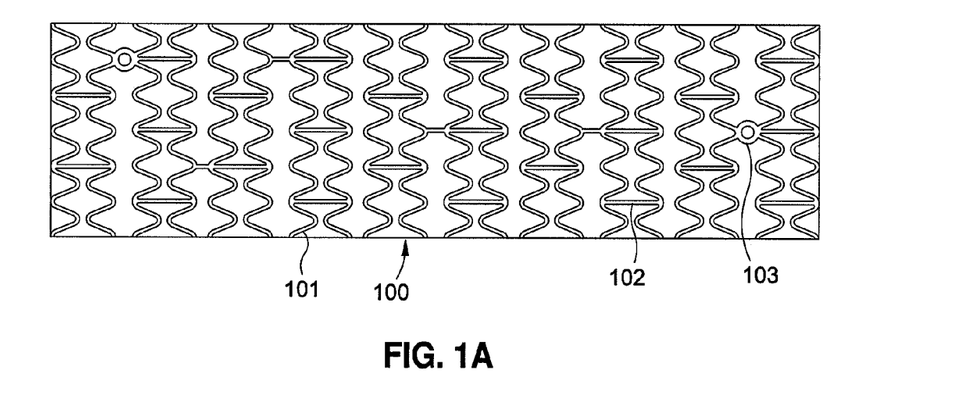
FIGS. 1A and 1B are pictorial diagrams of exemplary balloon expandable stents as an illustration of implantable medical devices in accordance with the preferred embodiment of the present invention.
Figure 1B:
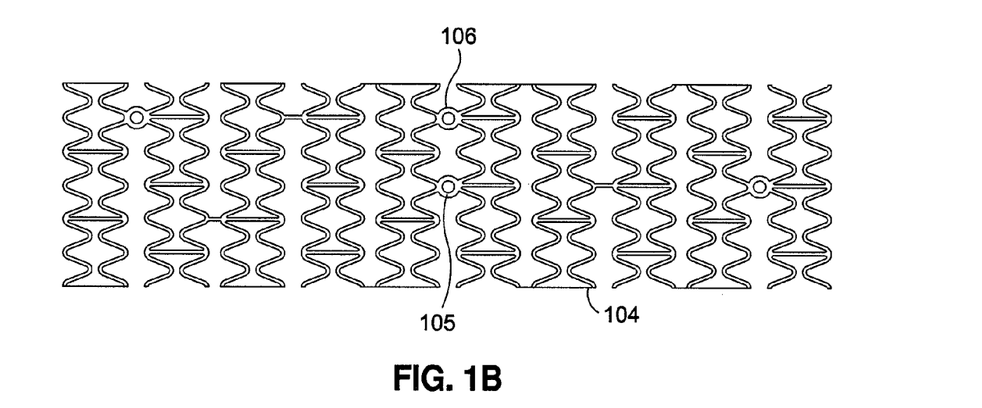

Referring to FIGS. 1A and 1B, there are provided two exemplary balloon expandable stent designs. FIG. 1A shows a tubular balloon expandable stent 100 with end markers 103 for further visibility. The stent 100 is composed of stent struts of a ring 101, ring connectors 102, and end markers 103. The stents 100 are made of multiple circumstantial rings 101, where the ring connectors 102 connect two or three adjacent rings 101 to hold the rings in place. For the end markers 103, a "disc" shaped marker is shown. The shape is not critical so long as the marker 103 can be used to add further visibility to the stents.

Referring to FIG. 1B, a tubular balloon expandable stent 104 is similar to the stent 100 shown in FIG. 1A except that the balloon expandable stent 104 comprises center markers 105, 106. The center markers 105, 106 help to locate an aneurysm opening during an implantation operation. The center markers can be of the same material and shape as the end markers.

Figure 2:
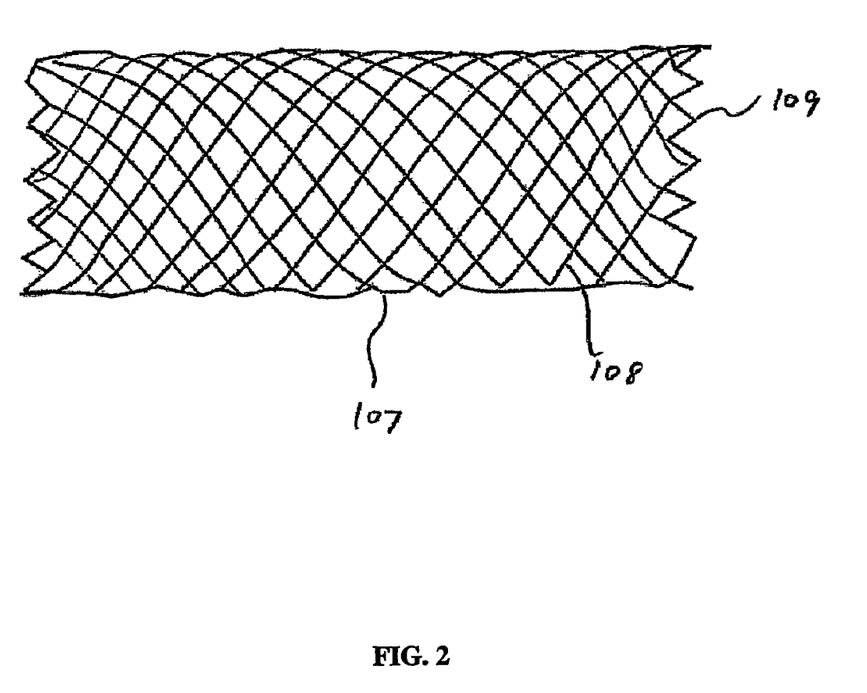
FIG. 2 is a pictorial diagram of a self-expanding stent as an illustration of implantable medical devices in accordance with the preferred embodiment of the present invention.

Referring to FIG. 2, there is provided a self-expanding stent 107 that is made of wires/ribbons. While a self-expanding stent may have many designs, the stent 107 having a typical braided pattern 108 with welded ends 109 is shown. The stent 107 is designed such that it is relatively flexible along its longitudinal axis to facilitate delivery through tortuous body lumens, but is stiff and stable enough radially in an expanded condition to maintain the patency of a body lumen, such as an artery when implanted therein.

Figure 3:
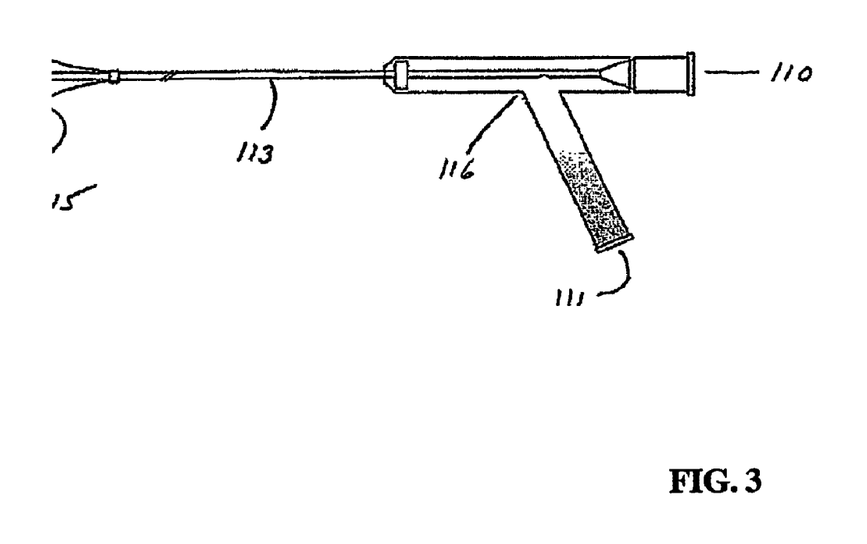
FIG. 3 is a pictorial diagram of a delivery system with a stent expanded onto the balloon in accordance with the preferred embodiment of the present invention.

Referring to FIG. 3, an expanded tubular stent 112 is shown. When the tubular stent 112 is fully expanded to its deployed diameter, the latticework of struts takes on a shape in which adjacent crests undergo wide separation, and portions of the struts take on a transverse, almost fully lateral orientation relative to the longitudinal axis of the stent. Such lateral orientation of a plurality of the struts enables each fully opened cell to contribute to the firm mechanical support offered by the stent in its fully deployed condition, to assure a rigid structure which is highly resistant to recoil of the vessel wall following stent deployment. It bears emphasis, however, that the configuration of this stent structure, while highly desirable, is illustrative only and not essential to the principles of the present invention.

While a stent may be deployed by radial expansion under outwardly directed radial pressure exertion, for example, by active inflation of a balloon of a balloon catheter on which the stent is mounted. The stent may be self-expandable. In some instances, passive spring characteristics of a preformed elastic (i.e., self-opening) stent serves the purpose. The stent is thus expanded to engage the inner lining or inwardly facing surface of the vessel wall with sufficient resilience to allow some contraction but also with sufficient stiffness to largely resist the natural recoil of the vessel wall.

The delivery system includes a guide wire lumen 110, a balloon inflating lumen 111, a connector 116, a balloon catheter shaft 113, and ring markers 115 on the catheter shaft 113. The guide wire lumen 110 is used for introducing a guide wire in a balloon catheter, and the balloon inflating lumen 111 for inflating the balloon after the stent to be placed reaches its targeted location. The connector 116 is used for separating the guide wire lumen 110 and the balloon inflating lumen 111. The balloon catheter shaft 113 carries the guide wire lumen 110 and the balloon inflating lumen 111 separately, with a typical length of about 135-170 cm. The ring markers 115 on the catheter shaft 113 is used for showing the start of balloon tapers and the edges of the stent.

Referring to FIG. 3, an expanded stent 112 is mounted onto an expanded balloon. The delivery catheter is a conventional balloon dilatation catheter used for angioplasty procedures. The balloon is formed of suitable materials such as irradiated polyethylene, polyethylene terephthalate, polyvinylchloride, nylon, and copolymer nylons such as Pebax™. Other polymers may also be used. In order for the stent to remain in place on the balloon during delivery to the desired site within an artery, the stent 112 is crimped onto the balloon.

In a preferred embodiment, the delivery of the stent 112 is accomplished in the following manner. The stent 112 is first mounted onto the inflatable balloon on the distal extremity of the delivery catheter. The stent 112 is mechanically crimped onto the exterior of the folded balloon. The catheter/stent assembly is introduced within vasculature through a guiding catheter. A guide wire is disposed across the diseased arterial section and then the catheter/stent assembly is advanced over a guide wire within the artery until the stent is directly under the diseased lining. The balloon of the catheter is expanded, engaging the stent against the inner surface of the artery. The expanded stent 112 maintains a fluid pathway through the artery after the catheter is withdrawn. Due to the formation of the stent from an elongated tube, the undulating component of the cylindrical elements of the stent is relatively flat in transverse cross-section, so that when the stent is expanded, the cylindrical elements are pressed into the wall of the artery and as a result do not interfere with the blood flow through the artery. The structural elements of the stent which are pressed into the wall of the artery will eventually be covered with endothelial cell growth which further minimizes blood flow interference. Furthermore, the closely spaced structural elements at regular intervals provide uniform support for the wall of the artery, and consequently are well adopted to tack up and hold in place small flaps or dissections in the wall of the artery.

For resilient or self-expanding prostheses, they can be deployed without dilation balloons or other stent expanding means. Self-expanding stents can be pre-selected according to the diameter of the blood vessel or other intended fixation site. While their deployment requires skill in stent positioning, such deployment does not require the additional skill of carefully dilating the balloon to plastically expand the prosthesis to the appropriate diameter. Further, the self-expanding stent remains at least slightly elastically compressed after fixation, and thus has a restoring force, which facilitates acute fixation. By contrast, a plastically expanded stent must rely on the restoring force of deformed tissue, or on hooks, barbs, or other independent fixation elements.

The open structure of the stent allows for a large portion of the vascular wall to be exposed to blood, which can improve the healing and repair of any damaged vessel lining. It is desirable that the stent struts be relatively thin in cross-section to minimize overall profile, yet have enough radial and tensile strength to maintain vessel patency after stent deployment. In order to achieve the radiopaque characteristics desired for clinical procedures, other stent designs must compromise some of the preferred characteristics by increasing the cross-sectional thickness of all the struts, increasing the cross-sectional thickness of some of the struts, or employing other materials for fabrication that fail to have the preferred characteristics of series 300 stainless steels. By fabricating a stent design with the unique alloy described herein, one can optimize the physical and mechanical parameters of the stent design for clinical utility without compromising the desired stent characteristics.

As discussed earlier, a stent must have enhanced visibility to assure that its movement and stay can be accurately monitored. Whether an object is radiopaque will depend on the thickness of the object, the material the object is made of, attenuation of radiation from surrounding materials and the energy of the radiation used to image the object. It also follows that for a given object, surrounding material and radiation energy, the material will be radiopaque at a thickness above a certain threshold and will be nonradiopaque at a thickness below the threshold. Importantly, for commonly used radiation (i.e., radiation energies of about 60-120 KeV), 316L is only radidpaque at a stent sidewall thickness above approximately 0.004 inches in vivo. Thus, stents made of 316L that have a sidewall thickness thinner than approximately 0.004 inches generally cannot be successfully imaged in the body using standard radiographic techniques. It is clear that while stainless steel alloys still enjoy its popularity in stent products with thick sidewalls, they are unable to produce stents that are strong, thin and with enhanced visibility.

Numerous attempts have been made to improve the visibility of stents made of stainless steel alloys. Some improvement has been achieved by applying a suitable adherent material layer to stent core material of medical grade implantable 316L stainless steel. Layer materials have included gold and certain other noble metals, such as platinum. For example, U.S. Pat. No. 6,623,520 discloses a composite stent having a substrate tube made of stainless steel, a nickel-cobalt-chromium-molybdenum alloy, or chonichrome with at least one metal cladding tube, where the metal cladding tube is made of platinum, gold, tantalum, tungsten, platinum-iridium, palladium, or nickel-titanium; U.S. Pat. No. 6,217,607 discloses a stent with a three-layer structure comprising a stainless steel layer, gold layer and iridium oxide layer, so that the stent can be used in its stent delivery system that is sized to allow it to traverse small-sized vessels in human body; U.S. Pat. No. 6,527,802 discloses a clad composite stent that comprises a central core and a case surrounding the core, where the core is formed of a radiopaque and relatively ductile material, e.g. tantalum or platinum, and the outer case of a relatively resilient material, e.g. a cobalt/chromium based alloy; and U.S. Pat. No. 6,508,832 discloses a stainless steel stent, which is substantially nickel-free and can be embodied in a substrate with one or more metallic cladding overlaying the substrate.

Such materials typically exhibit much greater radiopacity than stainless steel. They are also substantially non-allergenic and non-thrombogenic. Such coating may be provided in a very thin layer, to enable the stent sidewall thickness to be determined almost solely by considerations of mechanical strength. Coatings present a need for absolute adherence to the underlying metal of the stent to avoid cracking or defects in the homogeneous overlying layer, and sufficient resistance to peeling or flaking of the layer during insertion and especially during expansion of the diameter of the stent as it is being deployed into final position in the artery at the target site. These objectives are not easily achievable.

Some attempts were also made to incorporate radiopaque elements into stainless steel alloys in order to improve the visibility of stents. For example, WO 02/078764 discloses a stent that is made from a platinum-stainless steel alloy that has improved radiopacity relative to current utilized stainless steel alloys and preferably contains from about 2 wt. % to about 50 wt. % platinum, from about 11 wt. % to about 18 wt. % chromium, about 5 wt. % nickel and at least about 15 wt. % iron. U.S. Pat. No. 6,582,652 discloses an austenitic stainless steel series 300 alloy having improved biocompatible characteristics, where the alloy comprises C, Mn, Si, P, S, Cr, Mo, and platinum or tungsten, wherein the platinum or tungsten is about 5-10 wt. %.

The disadvantage of reduced mechanical strength of noble metals such as gold or platinum makes them unsuitable for sole use in the human vascular system.

Platinum:iridium (Pt/Ir), platinum:tungsten (Pt/W) and other platinum alloys possess excellent mechanical properties and enhanced visibility and biocompatibility are suitable for making implantable medical devices including stents. The strength of an alloy is critical for any stent, and determines the thickness of the sidewall of the stent. The stronger an alloy is, the thinner a stent can be made from the alloy. The strength of an alloy can be measured in many different tests, for example, for its ultimate tensile strength under conditions of annealed or stress relieved. Table 1 summarizes the ultimate tensile strength under conditions of annealed or stress relieved for Stainless steel 316L-BioDur®, Co—Cr:L605 NickelVac-TM, platinum, platinum:Iridium-90%:10%, platinum:Iridium-80%:20%, platinum:Iridium-70%:30%, platinum:Tungsten-92%:8%, Platinum:Nickel-90%:10%, platinum:Rhodium-70%:30%, and platinum:Rhodium:Ruthenium-79%:15%:6%.

TABLE 1

Ultimate tensile strength for different alloys.

| Alloy | Description Annealed-A Stress Relieved-SR | Ultimate tensile strength-Kpsi-Annealed | Ultimate tensile strength-Kpsi-Stress Relieved |
|---|---|---|---|
| SS: 316L-BioDur ™ | Tube (A), Wire/Ribbon (SR) | 85 | 150-200* |
| Co—Cr: L605-NickelVac ™ | Tube (A), Wire/Ribbon (SR) | 150 | 200-250* |

TABLE 1-continued

Ultimate tensile strength for different alloys.

| Alloy | Description Annealed-A Stress Relieved-SR | Ultimate tensile strength-Kpsi-Annealed | Ultimate tensile strength-Kpsi-Stress Relieved |
|---|---|---|---|
| Platinum | Tube (A), Wire/Ribbon (SR) | 24 | 60 |
| Platinum-Iridium-90%:10% | Tube (A) Wire/Ribbon (SR) | 60 | 150 |
| Platinum-Iridium-80%:20% | Same as above | 120 | 190 |
| Platinum:Iridium-70%:30% | Same as above | 160 | 270 |
| Platinum:Tungsten-92%:8% (#479) | Same as above | 130 | 185 |
| Platinum:Nickel-90%:10% | Same as above | 130 | 200 |
| Platinum:Rhodium-70%:30% | Same as above | 74 | 160 |
| Platinum:Rhodium:Ruthenium-79:15:6 | Same as above | 95 | 200 |

Notes:
Source: Johnson Mathey Medical, Sigmund Cohn Corp. and MatWeb.com
*estimates from various cold worked data sheets Annealed tubes are generally used for making balloon expanded stents, where elongation is an important aspect. Typically elongation at break is greater than 20%. Spring like, stress relieved wires or ribbons can be used to fabricate self-expanding stents. Typical elongation at break is between 1.5-3%.

Both types of stents may be fabricated using platinum alloys. Further processing may be needed to make stent surfaces smooth burr free and inert to the blood or body fluids.

Processing of the alloy is controlled to alleviate concerns over dimensional control of the final thickness of the foil and over maintaining its grain size. Welded tubes made from this alloy are preferably used to fabricate stents, which are made by rolling foil into a tube, laser-welding the seam, then drawing it to the required diameter of the stent. A chemical etching process is used, which requires tubes of consistent sidewall thickness and grain size in order to produce implant grade medical products.

No special techniques are required in melting, casting, or working the alloy for fabricating the stent. Induction heating is the preferred method of melting and refining the alloy used in fabricating the stent. Arc melting followed by argon-oxygen decarburization is another method of melting and refining, but other practices can be used. In addition, this alloy can be made using powder metallurgy techniques, if desired. This alloy is also suitable for continuous casting techniques.

Stents are typically formed from a cylindrical metal mesh from one of the alloys described herein by using various manufacturing techniques. Alternatively, they can be formed by a wire wrapped into a cylindrical shape. In the preferred embodiment, the stent is manufactured from a thin-walled tube, which is then laser cut to provide the desired configuration. The tube may also be chemically etched or electrical discharge machined (EDM) to form the desired configuration. In an alternative embodiment, the stent may be made from a flat pattern which is then formed into a tubular shape by rolling the pattern so as to bring the edges together. The edges may then be joined as by welding or the like to provide a desired tubular configuration. In addition, a thin tubular structure can be made by using magnetron sputtering as disclosed in U.S. Pat. No. 6,533,905, and the thin tubular structure may then be processed into stents by any known methods.

The stent may be fabricated using Ptir alloy as described earlier. The alloy can be received in a shape of a wire. This wire is shaped in belts of cylindrical shape and the belts are laser welded to one another at a specific points to join with each other (see FIGS. 1 and 2, for example).

This method enables a stent to be made that is very radiopaque (using the most visible Ptir alloy), having enhanced mechanical properties and biocompatibility. This also overcomes some manufacturing limitations of Ptir alloys in terms of their surface finishing. That is, the wire is prefabricated with close to perfect roundness surface quality. In contrast, laser cut tubing made from these alloys has proven to be difficult to treat including traditional electropolishing used for stainless steel.

All other stent properties including flexibility, radial strength, low profile are attainable relative to traditional alloys used for producing stents.

There are several manufacturing techniques which can transform a tubular member into a particular stent design: 1) photo-mask and etch techniques as described in U.S. Pat. No. 5,902,475; 2) a laser ablation/etching process disclosed in U.S. Pat. Nos. 6,066,167; 6,056,776; 5,766,238; 5,735,893; 5,514,154 or 5,421,955; and 3) utilizing a laser to directly cut away metal and form the pattern into a tubular member. Any one of these manufacturing examples can be used to produce the stent with the radiopaque alloys.

In the photo mask and etch process the outer surface of a tubular member is uniformly coated with, e.g., a photosensitive resist. This coated tubular member is then placed in an apparatus designed to rotate the tubular member while the coated tubular member is exposed to a designated pattern of ultraviolet (UV) light. The UV light activates the photosensitive resist causing the areas where UV light is present to expose (cross-link) the photosensitive resist. The photo-sensitive resist forms cross-links where is it exposed to the UV light, thus forming a pattern of hardened and cured polymer which mimics the particular stent design surrounded by uncured polymer. The film is adaptable to virtually an unlimited number of intricate stent designs. The process from the apparatus results in the tubular member having a discrete pattern of exposed photosensitive material with the remaining areas having unexposed photosensitive resist.

The exposed tubular member is immersed in a resist developer for a specified period of time. The developer removes the relatively soft, uncured photosensitive resist polymer and leaves behind the cured photosensitive resist which mimics the stent pattern. Thereafter, excess developer is removed from the tubular member by rinsing with an appropriate solvent. At this time, the entire tubular member is incubated for a specified period of time, allowing the remaining photosensitive resist polymer to fully cure and bond to the surface of the processed tubular member.

The processed tubular member is then exposed to an electrochemical etching process, which removes uncovered metal from the tubular member, resulting in the final tubular member or stent configuration.

In an example of the laser/etching process, a tubular member is coated with a resist and placed in a rotatable collet fixture of a machine-controlled apparatus for positioning the tubular member relative to a laser. Then, according to the machine coded instructions, the tubing is rotated and moved longitudinally relative to the laser which is also machine controlled wherein the laser selectively removes the resistant coating on the tubular member by ablation. A stent pattern is formed on the surface of the tubular member that is created by a subsequent chemical etching process.

In an example of the direct laser method, a tubular member is placed in a collet fixture of a machine-controlled apparatus for positioning the tubular member relative to a laser. Then, according to the machine coded instructions, the tubing is rotated and moved longitudinally relative to the laser which is also machine controlled wherein the laser selectively ablates and removes metal forming the stent pattern.

The presence of a stent in a vessel tends to promote thrombus formation as blood flows through the vessel, which results in an acute blockage. In addition, as the outward facing surface of the stent in contact or engagement with the inner lining of the vessel, tissue irritation can exacerbate restenosis attributable to hyperplasia. The thrombosis and occlusion caused by the placement of the stent may be reduced or even eliminated by proper modification of the surface of the stent.

Surface modification of the stent to apply a desired coating such as iridium oxide or titanium nitrate may be achieved by vapor deposition or plasma deposition, or other conventional methods. Such modification may be used to give the stent a rough surface. Alternatively, the surface may be passivated only, by oxidation of the iridium for reduced immunoresponse and less throubogenicity. Other surface modification may include Ion Implantation process which forms a barrier to metal such as nickel to leach out.

In the evolution of stents, there have been developments in the field of stents coated with a layer of polymers. The polymeric materials are typically capable of absorbing and releasing therapeutic drugs. Examples of such stents are disclosed In U.S. Pat. No. 5,443,358 to Eury; U.S. Pat. No. 5,632,840 to Campbell; U.S. Pat. No. 5,843,172 to Yan; and U.S. Ser. No. 08/837,993, filed Apr. 15, 1997, by Yan.

Stents may be coated with one or more layers (coatings). The external surfaces and intratubular surfaces may have different coatings. The coatings may incorporate any desired substances including therapeutic substances, alone or in a carrier, so that the substances are released over time after implantation. The coatings usually employ polymers that include polycarboxylic acids; cellulosic polymers including cellulose acetate and cellulose nitrate; gelatin; polyvinylpyrrolidone; crosslinked polyvinylpyrrolidone; polyanhydrides including maleic anhydride polymers; polyamides; polyvinyl alcohols; copolymers of vinyl monomers such as EVA; polyvinyl ethers; polyvinyl aromatics; polyethylene oxides; polyesters including polyethylene terephthalate; polyacrylamides; polyethers; polyether sulfone; polycarbonate; polyalkylenes including polypropylene, polyethylene and high molecular weight polyethylene; halogenated polyalkylenes including polytetrafluoroethylene; polyurethanes; polyorthoesters; silicones; siloxane polymers; polylactic acid; polyglycolic acid; polycaprolactone; polyhydroxybutyrate valerate and blends and copolymers thereof; polypeptides; proteins including fibrin, collagen and derivatives thereof; glycosaminoglycans; polysaccharides such as celluloses, starches, dextrans, alginates and derivatives; hyaluronic acid; and squalene emulsions.

Therapeutic substances which can be delivered from stents include anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, anglostatin and thymidine kinase inhibitors; anesthetic agents such as lidocaine, bupivacaine, and ropivacaine; anticoagulants such as D-Phe-Pro-Arg chloromethyl keton, an RGD peptide-containing compound, heparin, antithrombin compounds, platelet receptor antagonists, antithrombin antibodies, anti-platelet receptor antibodies, aspirin, prostaglandin inhibitors, platelet inhibitors and tick antiplatelet peptides; vascular cell growth prornotors such as growth factor inhibitors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vascoactive mechanisms; anti-sense DNA and RNA; DNA coding for anti-sense RNA; tRNA or rRNA to replace defective or deficient endogenous molecules; angiogenic factors including growth factors such as acidic and basic fibroblast growth factors, vascular endothelial growth factor, epidermal growth factor, transforming growth factor $\alpha$ and $\beta$, platelet-derived endothelial growth factor, platelet-derived growth factor, tumor necrosis factor $\alpha$, hepatocyte growth factor and insulin like growth factor; cell cycle inhibitors including CD inhibitors; thymidine kinase ("TK") and other agents useful for interfering with cell proliferation; the family of bone morphogenic proteins ("BMP's"); and BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP BMP-5, BMP-6 and BMP. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Stents or prostheses have been largely used in vascular structures including arteries and veins. Aside from vascular usage, other ducts or tracts of the human body in which a stent might be installed to maintain an open lumen include the tracheo-bronchial system, the biliary hepatic system, the esophageal bowel system, and the urinary tract. Many of the same requirements are found in these other endoluminal usages of stents.

Stents are used in many ways. For instance, stents have been used after atherectomy or standard balloon angioplasty to maintain acute and long-term patency of the vessel. Stents have also been used to overlie an aortic dissecting aneurysm, tack dissections to the vessel wall, eliminate the risk of occlusion caused by flaps resulting from the intimal tears associated with primary interventional procedure, or prevent elastic recoil of the vessel. Stents may be utilized in by-pass grafts as well, to maintain vessel patency. Stents can also be used to reinforce collapsing structures in the respiratory, biliary, urological, and other tracts.

Figure 4:
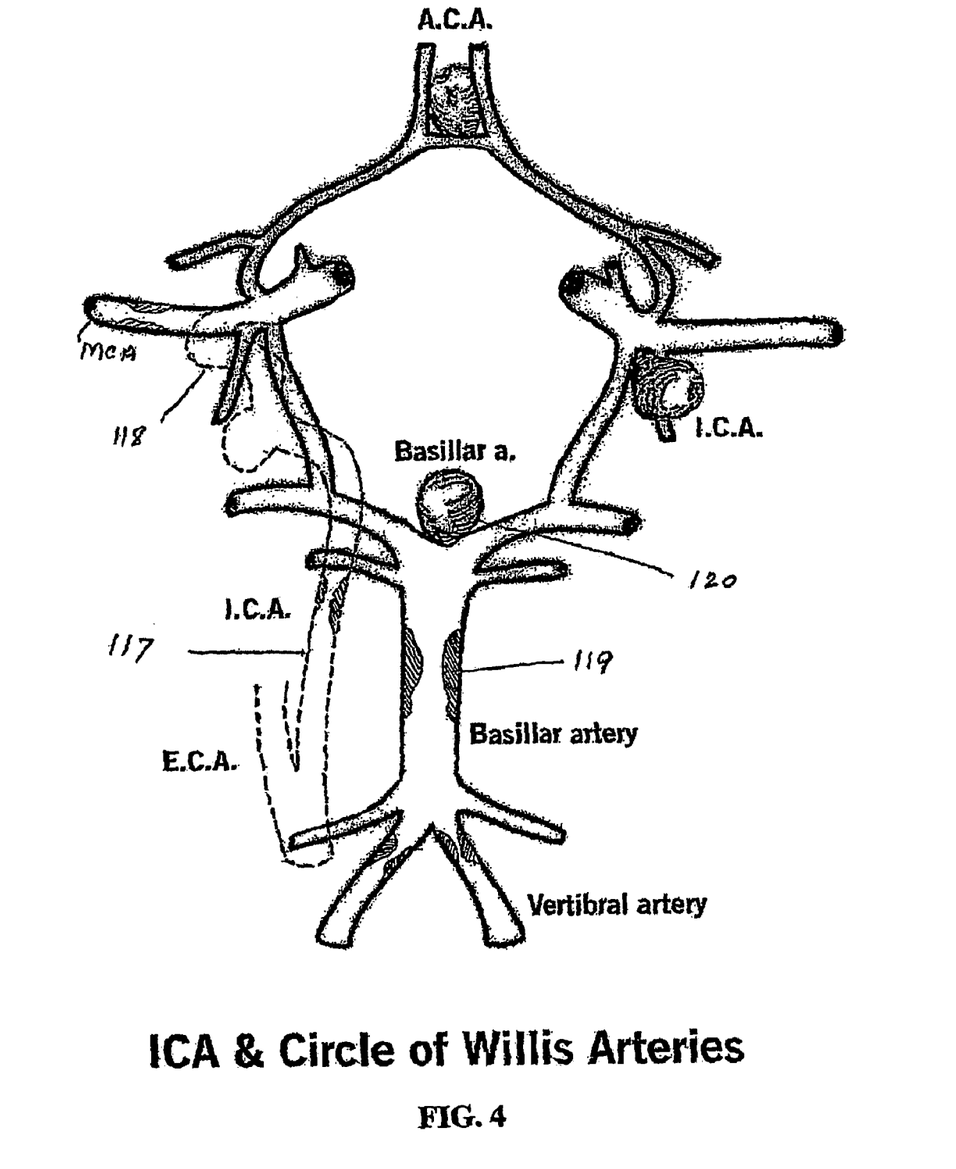
FIG. 4 is a pictorial diagram of the anatomy of arteries in the brain showing ischemia and aneurysms.

Referring to FIG. 4, a diagram of ICA and Circle of Willis (CW) arteries is shown. The stents are suitable for placement in small vascular structures such as of the brain. The internal carotid artery (ICA) 117 supplying blood to arteries such as the middle cerebral artery (MCA), and Circle of Willis. Also, vertebral arteries (VA) supplying blood to basilar (BA) and intracranial arteries through Circle of Willis are shown. Ischemic disease is shown in VA, ICA, BA and MCA. Aneurysms are shown on CW and ICA.

Access to small occluded arteries of the brain to allow adequate blood flow (Ischemic) or repairing a ruptured aneurysm is a highly desirable objective for treating millions of people who suffer from stroke each year. One of the technical prerequisites for successful treatment in these respects is the availability of a stent, and related delivery system, which is sufficiently small and thin that it can navigate and be deployed in these tiny vessels without occluding or damaging the lumen. It is also essential that the stent be highly visible during and after implantation to enable proper deployment and aftercare by the physician. The latter attribute is especially important for treatment of intracerebral arteries because of the obstacle to x-rays presented by the skull which makes precise visualization of a small thin stent extremely difficult. The stent should therefore be sufficiently radiopaque without need for its struts to be made so thick that the stent itself creates an unacceptable obstruction of the bodily vessel or too stiff to navigate through tortuous intracranial anatomy. Another prerequisite of a successful treatment of these extremely small diameter vessels is that the stent delivery system should be highly flexible to allow it to be advanced along the anatomy of the cerebral circulation. In addition, the total stent delivery system must be of extremely small profile, to treat diseased intra-cranial arteries generally ranging from 1.5 mm to 5 mm.

The stents made from platinum:iridium, platinum tungsten and other platinum alloys are strong with very thin sidewalls. In certain embodiments, the sidewalls of the stents are thinner than 0.0028". In certain embodiments, the sidewalls of the stents are about 0.0012" to 0.0028". Therefore, these stents and delivery systems are able to be used to enhance cerebral circulation.

In one example, an intracranial stent is specially designed for low pressure deployment. The stent has adequate radial strength for targeting a specific environment of fragile intracranial vessel. The stent is designed to allow for delivering high stent performance and absolutely conforming longitudinal flexibility. The stent may be made from any suitable alloy such as Stainless Steel, CoCr, Ptir, or PtW.

Low pressure deployment of a stent is defined as a pressure equal to or below 4 atm. This level of pressure enables the stent to be fully deployed to support stenosed intracranial vessel or aneurysm neck without introducing trauma or rapture of a target vessel. The stent can be deployed using balloon techniques and also may be self-expandable.

The stent comprises structural elements that restrict potential over expansion, matching the inner diameter of the vessel and to make deployment extremely precise. This feature of the structural elements in combination with low pressure deployment potentially reduces vessel injury, rupture or restenosis.

The stent also has longitudinal flexibility equal to or better than what is provided by a delivery catheter. This means that the stent does not add increased rigidity to the device. The trackability of the stent depends entirely on the mechanical properties of the catheter and is not restricted by stent alone. The longitudinal flexibility of the stent can be measured by force in grams to deflect the stent from neutral line. This force brings stent deflection to 1 mm for less than 8 grams. Existing catheters can provide 20-22 grams per 1 mm deflection. This condition is also extremely important when creating stent compliance to particular vessels and saves the vessel from possible traumatic reaction.

The structure of the stent is designed to provide a normalized radial force of 18-19 grams/mm of length and may reach values close to the ones found in existing coronary stents. Stent structural support provides 3-4% of deflection of stent structure in concert with intracranial vessel wall natural pulsing. This leads to greater stent conformity and vessel injury score reduction.

Intracranial stent has profile in compressed delivery mode 0.020"

Intracranial Stent is designed to be compressed onto delivery catheter with a profile as low 0.014"-0.016" having stent profile 0.020"-0.022".

Intracranial Stent with even material distribution and wall coverage, creating needed vessel support. Material ratio is in the range of 12-16% depending on deployment diameter.

Intracranial Stent having struts' thickness and width not larger then 0.0028". Struts' dimensions making the least intrusive stent material volume reducing vessel injury score.

Stent surface to length ratio is set to be 1.1-1.3 $mm^2$/mm to provide minimal vessel injury score.

It will be appreciated by persons skilled in the art that numerous variations and/or modifications may be made to the invention as shown in the specific embodiments without departing from the scope or spirit of the invention as broadly described. The present embodiments are, therefore, to be considered in all respects illustrative and not restrictive.

We claim:

1. A stent for insertion into a bodily vessel for treatment of an aneurysm or ischemic diseases,
    wherein the stent is made from a platinum:rhodium:ruthenium alloy comprising a composition of about 75-80% of platinum, 12-18% of rhodium and 5-10% of ruthenium;
    wherein the stent comprises a generally tubular structure having an exterior surface defined by a plurality of interconnected struts having a plurality of interstitial spaces therebetween, the stent having a sidewall thickness between about 0.0012 inches and 0.0028 inches;
    wherein the plurality of interstitial spaces have been cut from a sheet of metal forming the stent;
    wherein the stent is sized to be positioned entirely within an intracranial vessel; and
    wherein the stent comprises a self-expandable latticework of struts, the struts being interconnected to form a plurality of rings, the stent further comprising first ring connectors and second ring connectors, the first ring connectors connecting only two adjacent rings, the two adjacent rings being axially spaced relative to each other, the second ring connectors connecting only three adjacent rings, the three adjacent rings being axially spaced relative to each other, wherein at a given circumferential position of the stent, all of the first and second ring connectors are axially spaced from each other, the struts (i) each having a thickness and width of less than 0.0028 inches, (ii) providing even wall coverage along the length of the stent, and (iii) providing a stent surface to length ratio from 1.1-1.3 $mm^2$/mm, such that the stent expands with a force equal to or less than 4 atm and has a flexibility such that deflection of 1 mm from a neutral line occurs with less than 8 grams of force.

2. The stent according to claim 1, wherein said generally tubular structure is expandable from a first position to a second position, wherein said tubular structure expands radially outwardly to the second position such that the exterior surface of said structure engages with the inner surface of the bodily vessel so as to maintain a fluid pathway through said bodily vessel.

3. The stent according to claim 1, wherein the surface of the stent is modified by passive coatings.

4. The stent according to claim 3, wherein the coating comprises iridium oxide or titanium nitrate.

5. The stent according to claim 3, wherein the stent is coated with an external layer containing a pharmaceutically effective amount of therapeutic substances.

6. The stent according to claim 1, further comprising markers to enhance visibility and radiopacity of the device.

7. The stent according to claim 6, wherein the markers include end markers or center markers.

8. A delivery system for inserting a stent according to claim 1, within a bodily vessel, wherein the stent is self-expandable, the delivery system comprising a delivery catheter and the stent, wherein the stent is mounted onto a distal portion of the delivery catheter.

9. A stent according to claim 1, wherein the stent comprises a material ratio in the range of about 12% to about 16%.

10. A stent according to claim 1, wherein the stent has a profile of about 0.020 inches in compressed delivery mode.

11. A stent for insertion into a bodily vessel for treatment of an aneurysm or ischemic diseases,
wherein the stent is made from a platinum:rhodium alloy comprising a composition of about 65-75% of platinum and 25-35% of rhodium;
wherein the stent comprises a generally tubular structure having an exterior surface defined by a plurality of interconnected struts having a plurality of interstitial spaces therebetween, the stent having a sidewall thickness between about 0.0012 inches and 0.0028 inches;
wherein the plurality of interstitial spaces have been cut from a sheet of metal forming the stent;
wherein the stent is sized to be positioned entirely within an intracranial vessel; and
wherein the stent comprises a self-expandable latticework of struts, the struts being interconnected to form a plurality of rings, the stent further comprising first ring connectors and second ring connectors, the first ring connectors connecting only two adjacent rings, the two adjacent rings being axially spaced relative to each other, the second ring connectors connecting only three adjacent rings, the three adjacent rings being axially spaced relative to each other, wherein at a given circumferential position of the stent, all of the first and second ring connectors are axially spaced from each other, the struts (i) each having a thickness and width of less than 0.0028 inches, (ii) providing even wall coverage along the stent, and (iii) providing a stent surface to length ratio from 1.1-1.3 $mm^2$/mm, such that the stent expands with a force equal to or less than 4 atm and has a flexibility such that deflection of 1 mm from a neutral line occurs with less than 8 grams of force.

12. The stent according to claim 11, wherein said generally tubular structure is expandable from a first position to a second position, wherein said tubular structure expands radially outwardly to the second position such that the exterior surface of said structure engages with the inner surface of the bodily vessel so as to maintain a fluid pathway through said bodily vessel.

13. The stent according to claim 11, wherein the surface of the stent is modified by passive coatings.

14. The stent according to claim 13, wherein the coating comprises iridium oxide or titanium nitrate.

15. The stent according to claim 13, wherein the stent is coated with an external layer containing a pharmaceutically effective amount of therapeutic substances.

16. The stent according to claim 11, further comprising markers to enhance visibility and radiopacity of the device.

17. The stent according to claim 16, wherein the markers include end markers or center markers.

18. A delivery system for inserting a stent according to claim 11, within a bodily vessel, wherein the stent is self-expandable, the delivery system comprising a delivery catheter and the stent, wherein the stent is mounted onto a distal portion of the delivery catheter.

19. A stent according to claim 11, wherein the stent comprises a material ratio in the range of about 12% to about 16%.

20. A stent according to claim 11, wherein the stent has a profile of about 0.020 inches in compressed delivery mode.

* * * * *